US00PP22537P3

(12) United States Plant Patent
van Schie

(10) Patent No.: US PP22,537 P3
(45) Date of Patent: Feb. 28, 2012

(54) *GUZMANIA* PLANT NAMED 'SCHIELI'

(50) Latin Name: ***Guzmania* hybrid**
Varietal Denomination: Schieli

(76) Inventor: Hubertus van Schie, Delfgauw (NL)

( * ) Notice: Subject to any disclaimer, the term of this patent is extended or adjusted under 35 U.S.C. 154(b) by 0 days.

(21) Appl. No.: 12/803,917

(22) Filed: Jul. 9, 2010

(65) Prior Publication Data

US 2012/0011630 P1 Jan. 12, 2012

(51) Int. Cl.
*A01H 5/00* (2006.01)

(52) U.S. Cl. ..... Plt./371

(58) Field of Classification Search ..... Plt./371
See application file for complete search history.

*Primary Examiner* — June Hwu
*Assistant Examiner* — Louanne Krawczewicz Myers
(74) *Attorney, Agent, or Firm* — Cassandra Bright

(57) ABSTRACT

A new and distinct *Guzmania* hybrid cultivar named 'SCHIELI' is disclosed, characterized by a compact plant form, yellow bracts with red tips and many leaves. The new variety is a *Guzmania*, and is normally used as an ornamental plant.

1 Drawing Sheet

Figure 1:
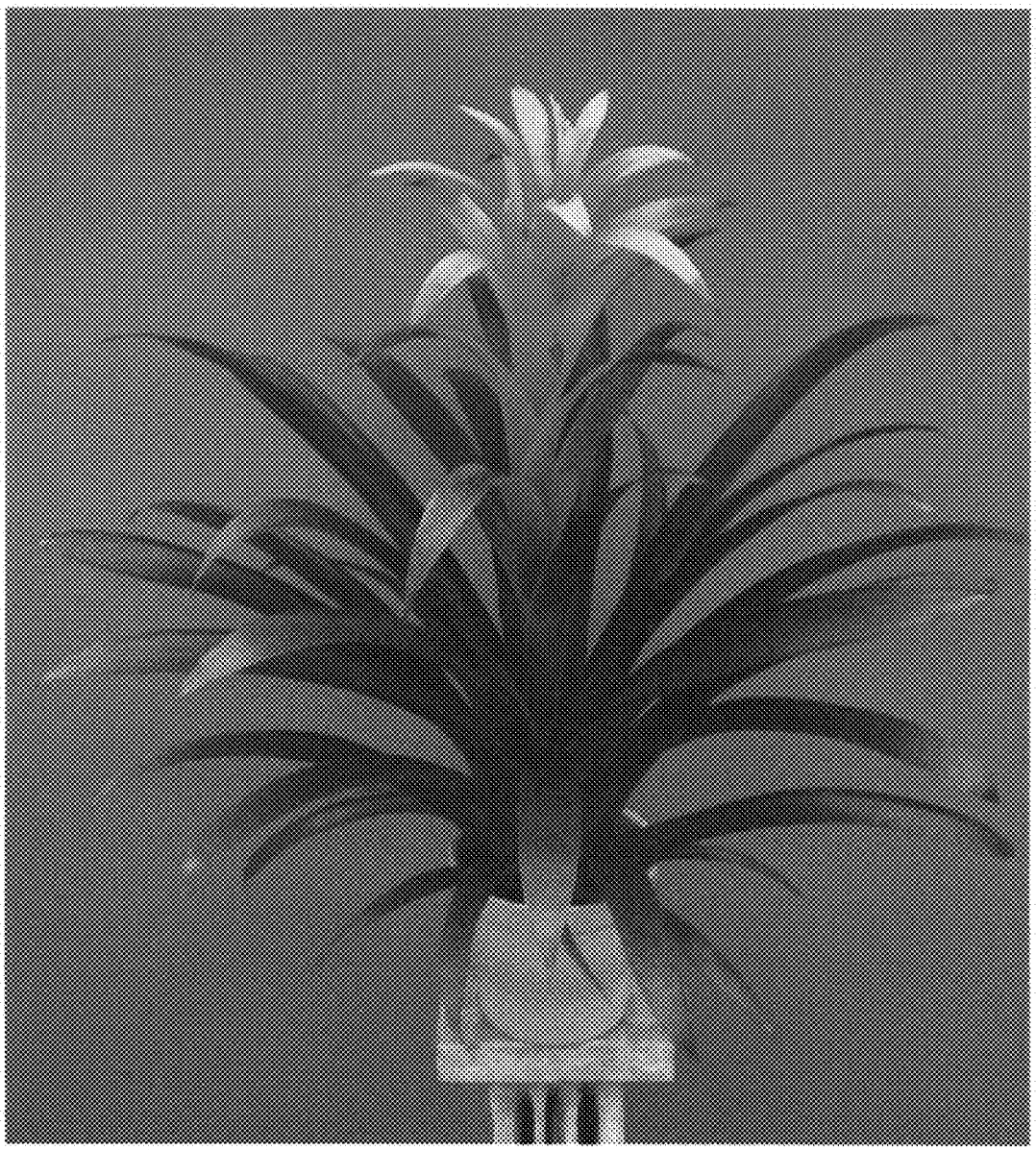

Latin name of the genus and species: *Guzmania* hybrid.
Variety denomination: 'SCHIELI'.

BACKGROUND OF THE INVENTION

The new cultivar is a product of a chance discovery. The new variety originated as a chance, whole plant mutation from the, unpatented, variety *Guzmania* hybrid 'Marjan.' The new variety was discovered by the inventor, Hubertus van Schie, a citizen of the Netherlands, in Delgauw, the Netherlands during 2004, in among a commercial planting of the parent variety.

Asexual reproduction of the new cultivar 'Schieli' was first performed in the Netherlands by tissue culture in 2004. 'Schieli' has since produced several generations by tissue culture and has shown that the unique features of this cultivar are stable and reproduced true to type.

SUMMARY OF THE INVENTION

The cultivar 'SCHIELI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SCHIELI.' These characteristics in combination distinguish 'SCHIELI' as a new and distinct *Guzmania* hybrid cultivar:

1. Yellow bracts with red tips
2. Compact plant form.
3. Many leaves.

PARENT COMPARISON

Plants of the new cultivar 'SCHIELI' are similar to plants of the parent variety, an *Guzmania* hybrid 'Marjan', in most horticultural characteristics. However, plants of the new cultivar 'SCHIELI' are more compact. Additionally, 'Marjan' typically has entirely yellow bracts, whereas the new variety has significant amounts of red in the bracts.

COMMERCIAL COMPARISON

Plants of the new cultivar 'SCHIELI' are similar to plants of the unpatented commercial variety, *Guzmania* hybrid 'Sunnytime' in most horticultural characteristics. However, plants of the new cultivar 'SCHIELI' are more compact than 'Sunnytime' and 'SCHIELI' produces bracts with more red than 'Sunnytime.'

BRIEF DESCRIPTION OF THE PHOTOGRAPH

The accompanying photograph in FIG. 1 illustrates in full color a typical plant of 'SCHIELI' grown in a greenhouse. The pot size is a commercial 15 cm container. The plant shown is approximately 18 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'SCHIELI' plants grown in a commercial controlled greenhouse in Delfgauw, the Netherlands. Temperatures ranged from 20° C. to 28° C. night and day. No artificial light, photoperiodic treatments or chemical treatments were given to the plants. Measurements and numerical values represent averages of typical plant types.

Botanical classification: *Guzmania* hybrid 'SCHIELI'
Age of plant described: Approximately 1 year.
Container size of plant described: Approximately 12 cm.

PROPAGATION

Type of propagation typically used: Tissue culture
Time to initiate roots: About 70 days at approximately 20-28° C.
Time to produce a rooted cutting/liner: About 125 days at approximately 20-28° C.
Root description: Moderately dense, moderately branched, fine, fibrous, not fleshy, colored near RHS Grey 201C

PLANT

Growth habit: Upright, monopodial
Height: Average: 42.7 cm
Plant spread: Average: 65.5 cm
Normal pot size: 12 cm
Growth rate: Moderate
Branching characteristics: Monopodial, leaves form a basal rosette, inflorescence grows from the center of the rosette
Number of leaves per scape: Average: 26
Stem length: No stems present, scape grows directly from rosette

FOLIAGE

Leaf:
*Arrangement.*—Rosulate; leaves (average: 26) placed in a basal rosette.
*Average length.*—Approximately 34.8 cm.
*Average width.*—Approximately 4.2 cm.
*Shape of blade.*—Ligulate.
*Aspect.*—Arching downward.
*Apex.*—Apiculate.
*Base.*—Sheathing. Sheath length: Average 6.8 cm. Sheath width: Average 7.9 cm. Sheath color: Near RHS Yellow-Green 152B.
*Margin.*—Entire.
*Texture of top surface.*—Smooth, very glossy.
*Texture of bottom surface.*—Smooth, very glossy.
*Color.*—Young foliage upper side: Near RHS Yellow-Green 145A. Young foliage under side: Near RHS Yellow-Green 145B. Mature foliage upper side: Near RHS Green N137A. Mature foliage under side: Near RHS Yellow-Green 146A.
*Venation.*—Type: Parallel. Venation coloration: Near RHS Green N137A.
Petiole: No petioles present, leaves sheathing

INFLORESCENCE

General description:
*Inflorescence height, excluding scape.*—Approximately 12.0 cm.
*Inflorescence width.*—Approximately 23.7 cm.
*Flowers.*—To date, flower development has been observed on plants of the new *Guzmania*.

Scape:
*Length.*—Approximately 26.0 cm.
*Width.*—Approximately 1.2 cm.
*Aspect.*—Approximately 90° angle to rosette (near vertical).
*Strength.*—Very strong.
*Color.*—Near RHS Yellow-Green 150C.
*Texture.*—Smooth.
Bracts:
*Scape/lowermost bracts.*—Shape: Ligulate. Length: Approximately 18.4 cm, excluding sheath. Width: Approximately 2.8 cm. Texture: Smooth.
*Quantity.*—Average 8.
*Tip.*—Apiculate.
*Base.*—Sheathing. Sheath length: Approximately 7.2 cm. Sheath width: Approximately 3.6 cm. Sheath color: Near RHS Yellow-Green 146D.
*Margin.*—Entire. Color Upperside: Upper half of the leaf blade near RHS Green N137A, lower half of the leaf blade near RHS Orange-Red 31A. Color Underside: Upper half of the leaf blade near RHS Yellow-Green 147B, lower half of the leaf blade near RHS Orange-Red 33A.
Terminal bracts:
*Shape.*—Short ligulate to triangular.
*Length.*—Approximately 9.5 cm, excluding sheath.
*Width.*—Approximately 3.6 cm.
*Quantity.*—Average 19.
*Texture.*—Smooth.
*Tip.*—Acute.
*Base.*—Sheathing. Sheath length: Approximately 2.5 cm. Sheath width: Approximately 3.9 cm. Sheath color: Near RHS Yellow-Green 153D.
*Margin.*—Entire.
*Coloration terminal bracts.*—Upperside: Near RHS Yellow-Orange 23A, tip near RHS Orange-Red N34A. Underside: Near RHS Orange 25A, tinged with RHS Orange-Red 34B, tip near Red 45B.
Reproductive organs: As no true flowers have been observed to date, the reproductive organs have not been observed for description.

OTHER CHARACTERISTICS

Disease resistance: Neither resistance nor susceptibility to diseases or pests has been observed in this variety.
Drought tolerance and cold tolerance: Observed to tolerate temperatures to 40° C. without any negative effects. Temperature tolerance above this range has not been observed. Tolerance of cold temperatures has not been observed.
Fruit/seed production: Not observed.

What is claimed is:

1. A new and distinct cultivar of *Guzmania* plant named 'SCHIELI' as herein illustrated and described.

* * * * *